United States Patent
Peana et al.

(10) Patent No.: US 11,969,209 B2
(45) Date of Patent: Apr. 30, 2024

(54) INFORMATION HANDLING SYSTEM DISPLAY VISUAL AUGMENTATION SYSTEM AND METHOD

(71) Applicant: Dell Products L.P., Round Rock, TX (US)

(72) Inventors: Stefan Peana, Austin, TX (US); Todd E. Swierk, Austin, TX (US); Timoteo T. Lee Kang, Boise, ID (US)

(73) Assignee: Dell Products L.P., Round Rock, TX (US)

( * ) Notice: Subject to any disclaimer, the term of this patent is extended or adjusted under 35 U.S.C. 154(b) by 48 days.

(21) Appl. No.: 17/153,668

(22) Filed: Jan. 20, 2021

(65) Prior Publication Data

US 2022/0225871 A1    Jul. 21, 2022

(51) Int. Cl.
| | |
|---|---|
| G09G 5/02 | (2006.01) |
| A61B 3/00 | (2006.01) |
| A61B 3/032 | (2006.01) |
| G09G 5/00 | (2006.01) |
| G16H 20/40 | (2018.01) |
| G16H 50/30 | (2018.01) |

(52) U.S. Cl.
CPC ............ *A61B 3/032* (2013.01); *A61B 3/0008* (2013.01); *A61B 3/0025* (2013.01); *A61B 3/0058* (2013.01); *G09G 5/006* (2013.01); *G09G 5/02* (2013.01); *G16H 20/40* (2018.01); *G16H 50/30* (2018.01); *G09G 2320/066* (2013.01); *G09G 2320/0666* (2013.01); *G09G 2354/00* (2013.01)

(58) Field of Classification Search
None
See application file for complete search history.

(56) References Cited

U.S. PATENT DOCUMENTS

| 8,913,004 B1* | 12/2014 | Bozarth | G06F 1/3234 |
| | | | 348/78 |
| 10,977,815 B1* | 4/2021 | Chao | G06F 3/013 |
| 10,984,751 B2 | 4/2021 | Peana | |
| 2015/0070406 A1 | 3/2015 | Baek | |
| 2015/0141763 A1* | 5/2015 | Roth | A61B 5/6821 |
| | | | 600/301 |
| 2015/0243052 A1 | 8/2015 | Park | |

(Continued)

OTHER PUBLICATIONS

Sciencedaily,"Declining Eyesight Improved by Looking at Deep Red Light," downloaded from https://www.sciencedaily.com/releases/2020/06/200629120241.htm on Nov. 15, 2021, 3 pages.

(Continued)

*Primary Examiner* — Kyle Zhai
(74) *Attorney, Agent, or Firm* — ZAGORIN CAVE LLP; Robert W. Holland

(57) ABSTRACT

End user interactions at a display are monitored for predetermined conditions to provide augmentation of display presentation by a red light that illuminates in the 650 to 800 nm range, such as at substantially 670 nm. Instructions stored in non-transient memory and executed on a processor present visual images of varied color contrast and evaluate end user inputs to determine an end user visual acuity. Over time and use of the display and red light, end user visual acuity is periodically tested to evaluate the effectiveness of red light illumination to restore visual acuity.

10 Claims, 5 Drawing Sheets

(56) References Cited

U.S. PATENT DOCUMENTS

| | | |
|---|---|---|
| 2016/0307541 A1 | 10/2016 | Kagaya |
| 2018/0137837 A1 | 5/2018 | Peana |
| 2018/0157035 A1 | 6/2018 | Fujita |
| 2020/0101290 A1* | 4/2020 | Rockley ............. A61N 1/36046 |
| 2021/0082371 A1 | 3/2021 | Novelli |
| 2021/0145276 A1* | 5/2021 | Yao ........................ G03B 30/00 |

OTHER PUBLICATIONS

Careueyes, "Blue Light Filter for PC," downloaded from https://care-eyes.com/ on Nov. 15, 2021, 8 pages.

F.Lux, "Software to Make Your Life Better," downloaded from https://justgetflux.com/ on Nov. 15, 2021, 2 pages.

Iris,"The World's Best Blue Light Filter and Eye Protection Software," downloaded from https://iristech.co/ on Nov. 15, 2021, 7 pages.

Microsoft, "Set Your Display for Night Time in Windows," downloaded from https://support.microsoft.com/en-us/windows/set-your-display-for-night-time-in-windows-18fe903a-e0a1-8326-4c68-fd23d7aaf136 on Nov. 15, 2021, 3 pages.

McCarthy, J., "One in Five U.S. Adults Use Health Apps, Wearable Trackers," Gallup, Dec. 11, 2019, downloaded from https://news.gallup.com/poll/269096/one-five-adults-health-apps-wearable-trackers.aspx on Nov. 15, 2021, 7 pages.

Wartella, E., "As Kids' Screen Time Surges During the Pandemic, Here's What Research Suggests," downloaded from https://www.forbes.com/sites/ellenwartella/2020/05/21/as-kids-screen-time-surges-during-the-pandemic-heres-what-research-suggests/?sh=7705239c5112#199066595112 on Nov. 15, 2021, 4 pages.

* cited by examiner

INFORMATION HANDLING SYSTEM DISPLAY VISUAL AUGMENTATION SYSTEM AND METHOD

BACKGROUND OF THE INVENTION

Field of the Invention

The present invention relates in general to the field of information handling system visual image presentation, and more particularly to an information handling system display visual augmentation system and method.

Description of the Related Art

As the value and use of information continues to increase, individuals and businesses seek additional ways to process and store information. One option available to users is information handling systems. An information handling system generally processes, compiles, stores, and/or communicates information or data for business, personal, or other purposes thereby allowing users to take advantage of the value of the information. Because technology and information handling needs and requirements vary between different users or applications, information handling systems may also vary regarding what information is handled, how the information is handled, how much information is processed, stored, or communicated, and how quickly and efficiently the information may be processed, stored, or communicated. The variations in information handling systems allow for information handling systems to be general or configured for a specific user or specific use such as financial transaction processing, airline reservations, enterprise data storage, or global communications. In addition, information handling systems may include a variety of hardware and software components that may be configured to process, store, and communicate information and may include one or more computer systems, data storage systems, and networking systems.

Increased emphasis on working from home has resulted in greater reliance on information handling systems for employee interactions, such as by having meetings through videoconferencing instead of in person. In many instances where employees would get a break from viewing information handling system displays to perform employment duties, such as word processing and computer aided design, by leaving screens to have discussions with other employees, now those discussions are also through screen interactions. Although remote interactions offer advantages in terms of work efficiency and isolating to prevent virus spread, the increased amount of screen time can create its own stress. For example, some studies have suggested that exposure to too much blue light in front of a display can produce uncomfortable side effects. Blue light is typically generated when images are defined by pixels of a display that mix red, green and blue light to create colors. The blue portion of the image component may be generated by light emitting diodes used as a backlight for a liquid crystal display (LCD) or organic light emitting diode (OLED) material of an OLED display. Some evidence suggests that over exposure to blue light in the 415 to 455 nm wavelength can produce retinal damage. Other evidence suggests that exposure to blue light in the 460 to 480 nm wavelength can impact melatonin production, which impacts sleep quality. Other evidence suggests that long term cumulative blue light exposure may lead to phototoxicity that can accelerate eye aging. These effects have led to some concern that the work from home situation faced by many employees could result in over exposure to blue light as screen time increases.

In particular, eye strain related to display screen tends to impact older end users. Current research indicates that human vision tends to decline with age, especially over the age of 40. As a result of age related visual decline, retinal sensitivity to light and peripheral color vision gradually weaken. Generally, declining vision is caused by aging mitochondria in cells that over time produce less energy in support of retinal cell functions. Additional research indicates that aging retina cells may benefit from exposure to certain types of light energy. For example, some observations indicate that exposing the retina to light waves spanning 650-800 nm can improve mitochondrial energy production. Tests performed on mice, bumblebees, fruit flies and humans show improvements in the function of a retina's photoreceptors when eyes are exposed to deep red light, such as 670 nm. One recent study published by Todd Kluss in June 2020 in the The Journals of Gerontology, Series A: Biological Sciences and Medical Sciences and entitled "Declining Eyesight Improved by Looking at Deep Red Light," indicated that individuals over 40 show improvements in cone color contrast sensitivity for color detection and rod sensitivity. This deep-red color spectrum light is not generally produced by light emitting diodes (LEDs) and organic light emitting diode (OLED) material used to create visual images at a display. Rather, other ranges of red spectrum light are generated and combined with blue and green light to provide the wide variety of colors presented at displays.

SUMMARY OF THE INVENTION

Therefore, a need has arisen for a system and method which provides information handling system display visual augmentation through red light exposure.

In accordance with the present invention, a system and method are provided which substantially reduce the disadvantages and problems associated with previous methods and systems to augment information handling system display visual image presentation. A red light source provides red light from a restorative spectrum range, such as 650 to 800 nm, at the display based upon one or more predetermined conditions and in response to instructions stored in persistent memory and executed on a processor. In one embodiment, the effectiveness of the red light treatment is evaluated by testing end user visual acuity based on recognition of visual images having variable color contrasts.

More specifically, an information handling system processes information with a processor that executes instructions and a memory that stores the information and instructions. A graphics processor further processes the information to define visual images with pixel values having colors for pixels to illuminate at a display. A red light source couples to the display to provide red illumination directed towards an end user in a restorative red light spectrum, such as 650-800 nm. For instance, the red light source includes a red LED that generates red light at substantially 670 nm and that is associated with positive effects on visual acuity. A red light manager stored in non-transitory memory and executed on a processor includes logic that presents a test of visual acuity to the end user, such as a displayed visual image of varied color and contrast that the end user interacts with to indicate the end user's ability to perceive color and contrast. Based upon end user interactions, a customized plan is developed to provide therapeutic red light illumination from the red light source, such as at a constant rate, at periodic intervals or in response to threshold exposure by the end user to the display or blue light presented at the display. The visual acuity test may be repeated, such as at a regular time interval or after a predetermined exposure to the display, so that the effectiveness of the restorative red light at helping visual acuity may be determined and optimized.

The present invention provides a number of important technical advantages. One example of an important technical advantage is that an end user receives restorative red light illumination that aids visual acuity, including automated suggestions for and application of the red light based upon exposure to visual images presented at the display. A test of visual acuity is provided to establish a base reference for an end user that is used as a basis for comparison against future tests of visual acuity to track the impact of display interactions on the end user. An end user is provided with a personalized plan for emitting red light as visual therapy and for tracking of visual acuity to evaluate and adapt the visual therapy.

BRIEF DESCRIPTION OF THE DRAWINGS

The present invention may be better understood, and its numerous objects, features and advantages made apparent to those skilled in the art by referencing the accompanying drawings. The use of the same reference number throughout the several figures designates a like or similar element.

DETAILED DESCRIPTION

An information handling system evaluates end user visual acuity at a display and selectively provides red light illumination as a visual therapeutic. For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communicating with external devices as well as various input and output (I/O) devices, such as a keyboard, a mouse, and a video display. The information handling system may also include one or more buses operable to transmit communications between the various hardware components.

Figure 1:
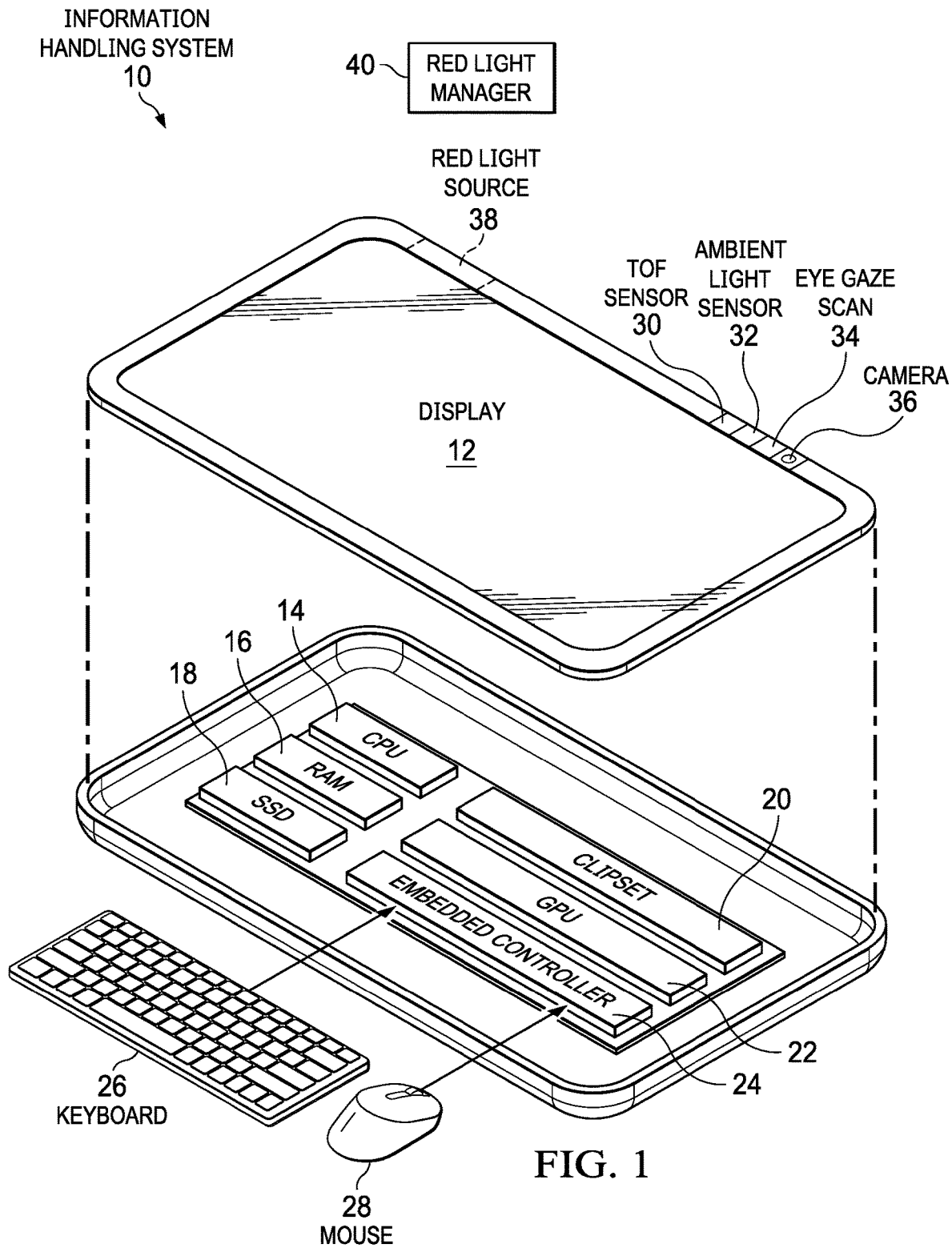
FIG. 1 depicts a block diagram of an information handling system having red light restorative exposure provided from a display.

Referring now to FIG. 1, a block diagram depicts an information handling system 10 having a red light restorative exposure provided from a display 12. Information handling system 10 processes information by executing instructions on a central processing unit (CPU) 14 that interfaces with a random access memory (RAM) 16 that stores the information and instructions. For example, a solid state drive (SSD) 18 or other non-transient memory provides persistent storage of an operating system and applications that are retrieved to RAM 16 at power up for execution at CPU 14. A chipset 20 interfaces with CPU 14 to manage processing operations, such as clock speed and memory accesses. A graphics processing unit (GPU) 22 processes the information to generate pixel values for communication to display 12, which presents the pixel values as a visual image. An embedded controller 24 interfaces with CPU 14 to manage physical operating conditions, such as power and thermal constraints, and to accept end user interactions through input devices, such as a keyboard 26 and mouse 28. In various embodiments, information handling system 10 may have a portable configuration with display 12 integrated in a housing or a desktop configuration with display 12 interfaced as a peripheral device. Further, information handling system 10 may interface with plural displays, including both integrated and peripheral displays.

In the example embodiment, display 12 integrates plural sensors that detect end user viewing conditions. For example, a time of flight sensor 30 determines end user presence and end user distance from display 12. An ambient light sensor 32 detects ambient light conditions, such as the color and brightness of environmental light conditions. An eye gaze sensor 34 determines a direction of an end user eye gaze, such as by comparing reflections of infrared light from an end user's eyes. A camera 36 captures visual images of an area in front of display 12, such as to support videoconference for a viewer of display 12. Information gathered from these display sensors is provided to embedded controller 24 and/or CPU 14 to support operational functions, such adjusting the brightness and color presented at display 12 based upon environmental conditions, controlling presentation at display 12 based upon user presence and accepting inputs from display 12 based upon a direction of an end user gaze.

A red light source 38 integrates with display 12 to provide illumination with restorative red light spectrum energy towards an end user under the control of a red light manager 40. For example, red light source 38 is a light bar that couples to the top of display 12 and includes LEDs that create red light in the 650-800 nm red light spectrum, such as at substantially 670 nm. These deep red light illuminations have a restorative effect for the human eye. Red light manager 40 monitors environmental conditions, such as ambient light conditions and end user presence in front of the display, to selectively provide red light illumination at display 12. In one example embodiment, red light manager 40 is an operating system driver retrieved from SSD 18 at system power up that includes instructions to evaluate an end user visual acuity and to provide red light illumination based upon the end user visual acuity. Evaluations of changes in end user visual acuity from a base level determined at initial testing to subsequent tests performed over time provides feedback to customize a plan for red light illumination for an end user. For example, logic of red light manager 40 executes on CPU 14 to present visual images at display 12 with varied brightness and color contrast so that an end user may interact with the visual images to provide a basis for evaluating the end user's visual acuity. In one example embodiment, red light manager 40 performs visual acuity tests in a controlled environment by measuring ambient light and having the end user adjust lighting to achieve a repeatable test condition. Ambient light may also be adjusted by providing illumination from red light source 38 during a visual acuity test. Once a base reference test is performed and stored for an end user, follow on tests performed over time, such as at predetermined intervals, can evaluate effectiveness of supplemental red light illumination by red light source 38 as an aid to end user visual acuity. For example, based upon the visual acuity test results, a low level of red light may be constantly emitted from red light source 38 while the end user is present, red light may be emitted in predefined circumstances like display content and ambient lighting, and/or red light may be emitted at defined intervals. In one example embodiment, end users may control red light illumination with individual settings to further customize the end user experience.

Red light manager 40 may provide red light exposure to an end user based upon a variety of usage modes that vary based upon a recommended exposure of red light, a detected exposure of blue light, an amount of time present at a display, a particular end user's light sensitivity as determined by periodic tests, and other factors. For instance, a suggested red light energy exposure may be based upon an end user visual acuity, such as where a younger end user with strong visual acuity may benefit less from red light exposure than an older end user with weak visual acuity. As an end user views a display, recommended red light exposure amounts may be adjusted based upon display content, display blue light emission values, environmental illumination and based on customized analysis derived from end user visual acuity tests. In some situations, an end user may leave red light illumination on as desired so that red light may be provided based upon end user selection and suggested where the end user selection falls below a recommended amount, such as by management through a threshold set as a customizable value for each end user. In various embodiments red light may be provided in a burst or continuous mode. The red light may be a monochromatic emission, such as 670 nm, or include additional portions of the deep red visual light spectrum.

Figure 2:
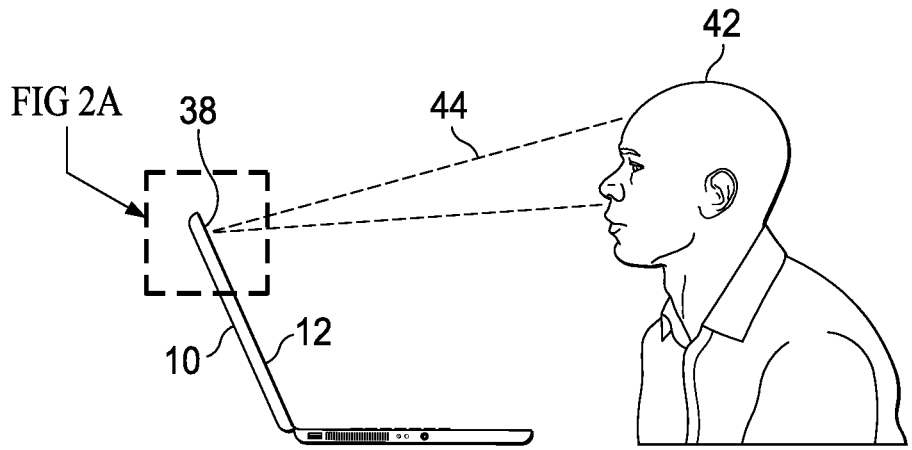
FIGS. 2 and 2A depict a side perspective view of red light exposure provided from an information handling system display.

Referring now to FIG. 2, a side perspective view depicts red light exposure provided from an information handling system display 10. In the example embodiment, end user 42 views a display 12 integrated in a portable information handling system 10. A red light source 38 integrates in portable information handling system 10 to direct a beam of restorative red light 44 towards the eyes of end user 42. In an alternative embodiment, red light source 38 may be provided from a peripheral display or as a separate light bar that couples and de-couples at the upper perimeter of a display. In one embodiment, restorative red light illumination may be integrated in a display panel so that the restorative red light is provided as part of the illumination from the display panel backlight. For example, although the deep red illumination is difficult to use for generating visual images by mixing with green and blue light, it can provide backlight illumination during inactive screen presentations, such as with a screen saver. By constantly emitting a low level of restorative red light from red light source 38, end user 42 has therapeutic levels of red light exposure that does not disrupt end user interactions or visual experience at display 12. In one embodiment, restorative red light illumination may be provided automatically or suggested by an message to the end user based upon the amount of blue light exposure that the end user experiences, such as is monitored by U.S. patent application Ser. No. 17/153,665, filed Jan. 20, 2021, entitled "Information Handling System Blue Light Exposure System and Method," by Todd Swierk, Stefan Peana and Tim Kang, which is incorporated herein as if fully set forth. For instance, when blue light exposure exceeds a threshold, therapeutic red light exposure is suggested to aid in end user recovery and eye health.

Figure 2A:
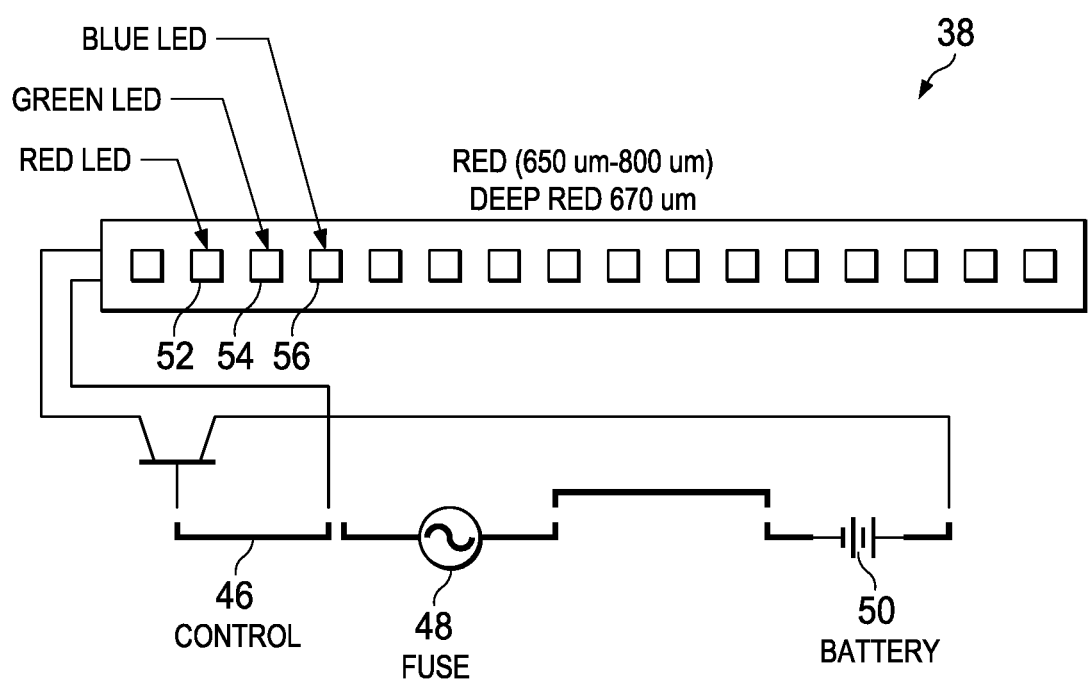

Referring now to FIG. 2A, an exploded view of information handling system 10 depicts an example of a red light source 38 configured to provide restorative red light illumination to an end user. The example embodiment is light bar that couples to a display with a controller 46 that communicates with an information handling system processor to accept commands that define illumination parameters. A fuse 48 interfaces a battery 50 with controller 46 to provide power; although alternative embodiments may have illumination powered from the display or information handling system. Red LEDs 52, green LEDs 54 and blue LEDs 56 are selectively illuminated to provide desired levels of illumination. For instance, a white light may be provided to assist an end user in reading material, and variations in color may be provided in combination with the restorative red light based upon end user preferences and customized settings. In one example embodiment, blue LED 56 may be replaced with alternative combinations of LED colors so that a white light is produced without using a blue LED.

Figure 3:
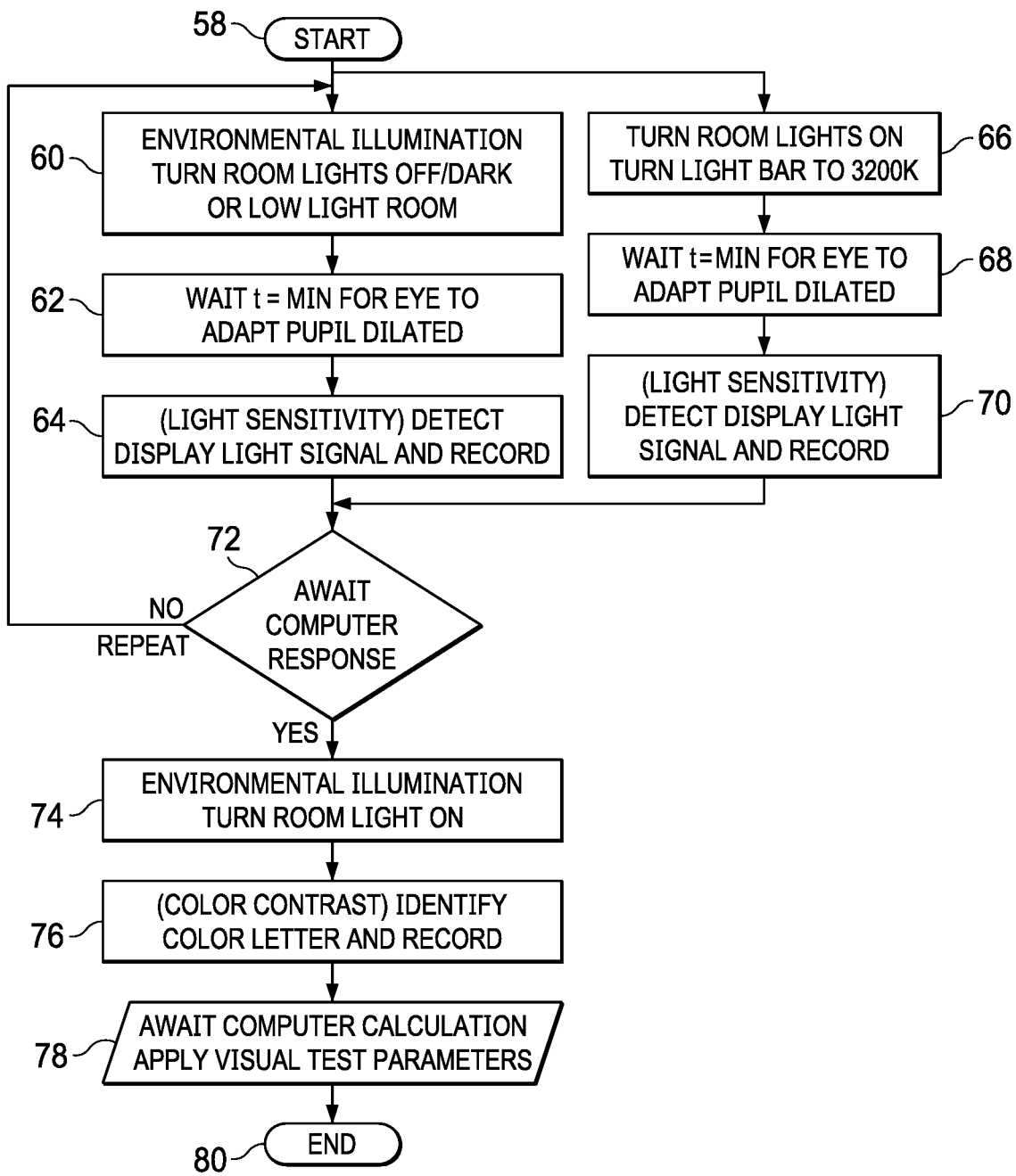
FIG. 3 depicts a flow diagram of a process for evaluating end user visual acuity at a display.

Referring now to FIG. 3, a flow diagram depicts a process for evaluating end user visual acuity at a display. The process starts at step 58 and forks to steps 60 and 66 to initiate the eye test. At step 60, environmental illumination is reduced, such as by automatically turning lights low or presenting a message instructing the end user to reduce lighting. At step 62, a wait time is applied to await dilation of the end user pupils, such as a preset time or a dynamically adjusted time computed from the initial sensed ambient light and expected time to achieve pupil dilation at the final sensed ambient light. At step 64, display light signals, such as visual images presented with variance in color contrast, are presented and end user interactions with the visual images are recorded. At step 66, the environmental lights are turned on and the red light source provides illumination with a color temperature of 3200K. At step 68, a time is applied to provide dilation of the pupils for the environmental light conditions. At step 70, visual images are presented at the display to allow end user interactions and store the end user inputs for evaluation of end user visual acuity. At step 72, the process returns to step 58 when the system has not completed evaluation of end user visual acuity. Once the evaluation is complete, the process continues to step 74 to return the environmental illumination to normal. At step 76, visual images are presented with varied color contrast in the environmental conditions and end user response is recorded. At step 78, the end user visual acuity is calculated across the low and high environmental light conditions and recorded for comparison at subsequent tests and the process ends at step 80.

Figure 4:
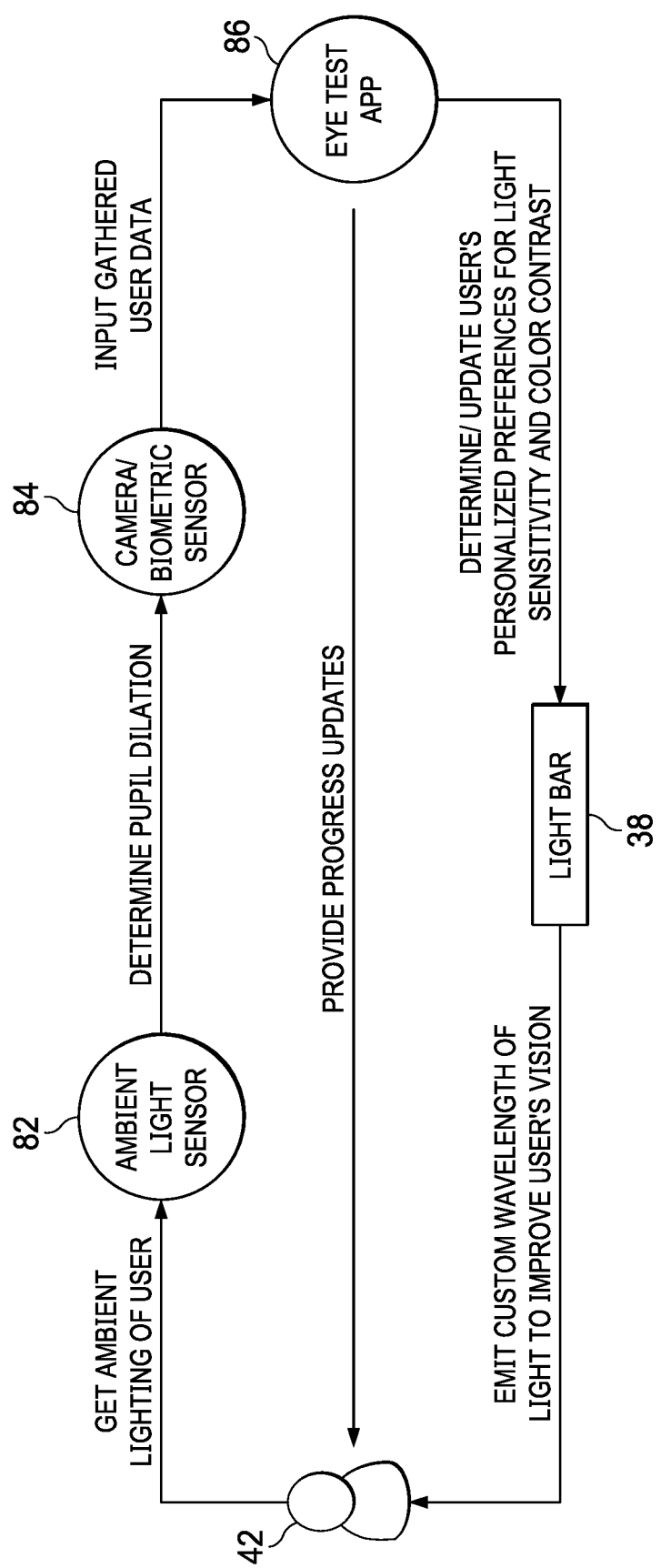
FIG. 4 depicts a high level system architecture for evaluation of visual acuity and the restorative impact of red light therapy.

Referring now to FIG. 4, a high level system architecture is depicted for evaluation of visual acuity and the restorative impact of red light therapy. The system addresses end user 42 visual acuity by establishing a base measurement of the end user's visual acuity, developing a plan for red light therapy and performing follow up tests of end user visual acuity to determine the effectiveness of the red light exposure on end user visual acuity. Ambient light conditions for end user 42 are measured by an ambient light sensor 32 and the end user pupil dilation for the test is confirmed by biometric sensor 84, such as a camera. Once the end user pupil dilation is confirmed, visual images presented at the display and end user interactions with the visual images provides information regarding the end user visual acuity that is evaluated by an eye test application 86. Based upon the eye test results, end user visual acuity is updated and applied to determine personalize preferences for light sensitivity and color contrast of the end user. These light preferences are applied to control illumination from red light source 38 when the end user is present so that therapeutic red light is provided at an appropriate level and for an appropriate amount of time at a custom wavelength that that aids the end user's vision.

Figure 5:
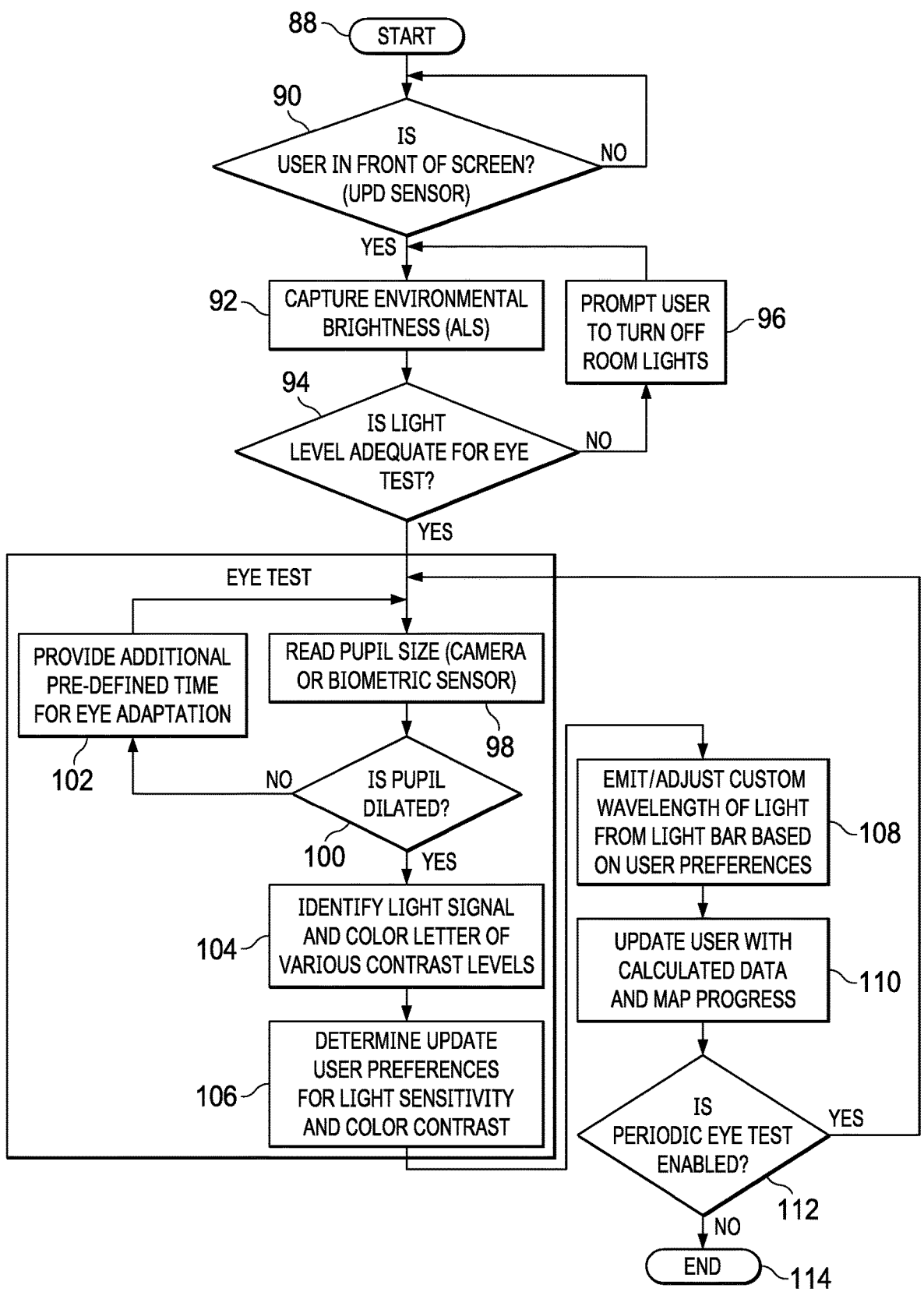
FIG. 5 depicts a flow diagram of a process for managing end user visual acuity with planned red light exposure therapy.

Referring now to FIG. 5, a flow diagram depicts a process for managing end user visual acuity with planned red light exposure therapy. The process starts at step 88, such as at power up of the system. At step 90 a determination is made of whether the end user is in front of the display screen, such as with a user presence detection device like a time of flight sensor or eye gaze sensor. If not, the process returns to step 88 to continue monitoring for end user presence. If an end user is present, the process continues to step 92 to capture ambient light conditions, such as ambient light brightness with an ambient light sensor. At step 94 a determination is made of whether the light level is adequate for an eye visual acuity test. If not, the process continues to step 96 to prompt the user to moderate the ambient lights, such as by turning off the room lights. At step 94, once ambient light conditions area adequate for performing eye visual acuity test, the process continues to step 98 to initiate the eye test, which encompasses steps 98-106. At step 98, the end user's pupil size is read, such as with a camera, eye gaze sensor or other biometric sensor. At step 100, a determination is made of whether the pupil is sufficiently dilated for the eye test. If not, the process continues to step 102 to provide additional time for eye adoption to the ambient light conditions. The wait time to return to step 98 may be a defined interval or may be estimated based upon the pupil size, the sensed ambient light conditions, and an estimate of rate of change of pupil dilation.

Once the pupil is determined to have sufficient dilation at step 100, the process continues to step 104 to identify for presentation to the end user light signals and color letters of various contrast levels for presentation to the end user as a test of the end user visual acuity. For example, a visual image may present a gradient of color contrast for a shape to judge where the end user sees the shape. As an alternative, a visual image of a minimal contrast has the contrast gradually increased until the end user recognizes the visual image, such as a letter. In another embodiment, visual images may be generated at the red light source with selective illumination of red, blue and green LEDs. At step 106, the end user inputs responsive to visual images presented as a test are evaluated to determine the end user visual acuity, such as visual preferences for light sensitivity and color contrast. The process then continues to step 108 to emit and adjust a custom wavelength of light from the red light source based upon the end user preferences and the results of the end user visual acuity test. At step 110, the end user is updated as to the results of the test with the calculated data and with graphical maps of the end user change in visual acuity from historical test data. At step 112, a determination is made of whether the end user has set up a periodic eye test to track end user visual acuity. If so, the process delays to the set interval and then returns to step 98. If not, the process completes and end at step 114.

Although the present invention has been described in detail, it should be understood that various changes, substitutions and alterations can be made hereto without departing from the spirit and scope of the invention as defined by the appended claims.

What is claimed is:

1. A method for augmentation of presentation of visual information at a display of an information handling system, the method comprising:
   processing information with an operating system and applications executing on a processor that generate the visual information;
   presenting the visual information as visual images at the display with illumination by the display, the visual images including active presentations and inactive presentations;
   monitoring end user interactions at the display with an operating system driver that evaluate end user visual acuity; and
   in response to a predetermined level of end user interactions, initiating red light illumination of red light with a red light source integrated in the information handling system display and having a 650 to 800 nm spectral range, the red light source separate from the illumination of the display associated with presentation of the visual images at the display, the red light source illumination presented when the visual information is inactive presentations.

2. The method of claim 1 wherein the red light emits at 670 nm.

3. The method of claim 1 wherein the red light comprises plural light emitting diodes (LEDs) of different colors, the method further comprising:
   selectively illuminating all of the plural LEDs to generate white light; and
   selectively illuminating only red LEDs of the plural LEDs to generate the red light.

4. The method of claim 1 wherein the monitoring interactions further comprises monitoring for eye gaze of the end user directed at the display.

5. The method of claim 1 wherein the monitoring interactions further comprises monitoring the end user distance to the display.

6. The method of claim 1 further comprising:
   performing plural tests over time of the end user's visual acuity by presenting visual images at the display having predetermined color contrast and evaluating the end user's inputs that indicate recognition of the color contrast; and
   evaluating the effect of the illumination of red light based upon changes in the end user's visual acuity over the time.

7. A system for augmenting display interactions, the system comprising:
   a light operable to present red light in a 650 to 800 nm spectral range;
   a non-transient memory storing instructions that, when executed on a processor, cause:
   monitoring of an end user's interactions at a display that presents information as visual images that include active presentations and inactive presentations, the display separate from the light; and
   illumination of the red light by the light at the display in response to one or more predetermined conditions including at least a predetermined level of the end user's interactions, the red light presented when the visual information is the inactive presentations and not when the visual information is the active presentations.

8. The system of claim 7 wherein the light further comprises:
plural light emitting diodes (LEDs) of different colors that simultaneously illuminate to create white light, at least one of the plural LEDs illuminating the red light; and
a controller operable to selectively command the white light and the red light.

9. The system of claim 7 wherein the instructions when executed on the processor further cause:
performing plural tests over time of the end user's visual acuity by presenting visual images at the display having predetermined color contrast and evaluating the end user's inputs that indicate recognition of the color contrast; and
evaluating the effect of the illumination of red light based upon changes in the end user's visual acuity over the time.

10. The system of claim 7 wherein the predetermined level of end user interactions comprises interactions measured by end user presence at the display and end user distance to the display.

* * * * *